(12) United States Patent
Peng et al.

(10) Patent No.: US 10,984,234 B2
(45) Date of Patent: Apr. 20, 2021

(54) METHOD AND APPARATUS FOR IMAGE RECOGNITION BASED ON RETINA PROSTHESIS

(71) Applicant: SHENZHEN CAS-ENVISION MEDICAL TECHNOLOGY CO., LTD, Shenzhen (CN)

(72) Inventors: Bo Peng, Shenzhen (CN); Saisai Zhao, Shenzhen (CN); Tianzhun Wu, Shenzhen (CN)

(73) Assignee: SHENZHEN CAS-ENVISION MEDICAL TECHNOLOGY CO., LTD, Shenzhen (CN)

(*) Notice: Subject to any disclaimer, the term of this patent is extended or adjusted under 35 U.S.C. 154(b) by 98 days.

(21) Appl. No.: 16/467,201

(22) PCT Filed: Dec. 6, 2016

(86) PCT No.: PCT/CN2016/108714
§ 371 (c)(1),
(2) Date: Jun. 6, 2019

(87) PCT Pub. No.: WO2018/102988
PCT Pub. Date: Jun. 14, 2018

(65) Prior Publication Data
US 2020/0082166 A1     Mar. 12, 2020

(51) Int. Cl.
*A61F 2/02*     (2006.01)
*A61F 2/14*     (2006.01)
(Continued)

(52) U.S. Cl.
CPC .......... *G06K 9/00496* (2013.01); *A61F 2/141* (2013.01); *A61F 9/08* (2013.01); *G06F 9/542* (2013.01)

(58) Field of Classification Search
USPC ............... 351/159.75–159.81; 382/114–128, 382/168–170, 181–224, 254–299
See application file for complete search history.

(56) References Cited

U.S. PATENT DOCUMENTS 9,205,257 B1 * 12/2015 Coley ..................... A61F 2/141
10,773,083 B2 * 9/2020 Greenberg ........... H04N 5/2252
(Continued)

FOREIGN PATENT DOCUMENTS

| CN | 101690687 A | 4/2010 |
| CN | 102509283 A | 6/2012 |

(Continued)

OTHER PUBLICATIONS

International Search Report dated Sep. 15, 2017 in corresponding International application No. PCT/CN2016/108714; 4 pages.

*Primary Examiner* — Marcellus J Augustin
(74) *Attorney, Agent, or Firm* — Maier & Maier, PLLC

(57) ABSTRACT

A method and an apparatus for image recognition based on a retina prosthesis. The method includes: recognizing meaning of an image captured; and converting the meaning of the image into a corresponding meaning prompt signal and transmitting the meaning prompt signal to a corresponding retina prosthesis electrode in connection with a retina. The method can effectively improve the problem that the existing retina prosthesis cannot recognize colors or complex scenes, enhance the recognition function of the retina prosthesis, and improve the quality of life of blind patients.

16 Claims, 4 Drawing Sheets

(51) Int. Cl.
  *A61F 9/00* (2006.01)
  *G06K 9/00* (2006.01)
  *A61F 9/08* (2006.01)
  *G06F 9/54* (2006.01)

(56) References Cited

U.S. PATENT DOCUMENTS

| | | |
|---|---|---|
| 2004/0186533 A1 | 9/2004 | Greenberg et al. |
| 2007/0016425 A1* | 1/2007 | Ward ................... G09B 21/003 704/271 |
| 2008/0021516 A1* | 1/2008 | Greenberg ......... A61N 1/36046 607/54 |
| 2011/0004271 A1* | 1/2011 | Dapper ................. A61N 1/025 607/53 |
| 2013/0035742 A1* | 2/2013 | Talbot ................ A61N 1/36046 607/54 |

FOREIGN PATENT DOCUMENTS

| | | |
|---|---|---|
| CN | 102657572 A | 9/2012 |
| CN | 103784251 A | 5/2014 |

* cited by examiner

METHOD AND APPARATUS FOR IMAGE RECOGNITION BASED ON RETINA PROSTHESIS

CROSS-REFERENCE TO RELATED APPLICATIONS

This application is a U.S. National Stage of International Patent Application No. PCT/CN2016/108714 filed on Dec. 6, 2016. The aforementioned application is hereby incorporated by reference in its entirety.

FIELD

The present application relates to the technical field of retina prosthesis, and more particularly to a method and an apparatus for image recognition based on a retina prosthesis.

BACKGROUND

With the development of biotechnology, it has become a target of more and more retina prosthesis R&D team product in design and production to improve the quality of life of blind patients. The existing retina prosthesis adopts the implanted microelectrode array to output corresponding electrical stimulation signal to retina neurons according to image information of the external environment.

A retina prosthesis typically includes camera sunglasses in vitro and a microelectrode array in vivo, and an ophthalmologist will implant the microelectrode array in vivo onto a patient's retina, with each electrode acting as a pixel in an image. The working principle is as follows, when an image is captured by the camera in vitro and transmitted to the microelectrode arranged on the retina prosthesis of the patient by radio signal, an electrical pulse will be emitted from the microelectrode to stimulate the imaging-related retina neuron in the eye, so as to form a contour of the image. For example, when a patient reads letters (SIAT), the retina prosthesis will output SIAT graphical information to the retina in the form of electrical pulses by the microelectrode array (as shown in FIG. 1). Similarly, when a patient encounters a person, the retina prosthesis outputs the overall contour of the person by the microelectrode array.

However, the resolution of the existing retina prosthesis is limited (the highest resolution of the current manner of implant onto the retina in the world is 60 channels), only the contour information of the external environment or object can be recognized, neither can the specific details be seen, nor can the colors be recognized, which limits the ability to reconstruct complex external visual information and is unable to help patients to quickly recognize complex scenes in a complex world.

SUMMARY

In order to solve the above problems in the prior art, it is an object of the present application to provide a method and an apparatus for image recognition based on a retina prosthesis, which can effectively improve the problem that the existing retina prosthesis cannot recognize colors or complex scene, enhance the recognition function of the retina prosthesis, and improve the quality of life of blind patients.

To achieve the above object, embodiments of the present application provide a method for image recognition based on a retina prosthesis, comprising: recognizing meaning of an image captured; and converting the meaning of the image into a corresponding meaning prompt signal and transmitting the meaning prompt signal to a corresponding retina prosthesis electrode in connection with a retina.

To above the above object, embodiments of the present application provides an apparatus for image recognition based on a retina prosthesis, comprising: a recognition module, configured to recognize meaning of an image captured; and a meaning transmission module, configured to convert the meaning of the image into a corresponding meaning prompt signal and transmitting the meaning prompt signal to a corresponding retina prosthesis electrode in connection with a retina.

It is known from the technical solutions provided by the above embodiments of the present application that the recognition of the color in the image, the facial feature, the specific object, and the relative spatial position, and other meanings helps to expand the user's ability to recognize complex scenes. When used together with the image area of the electrode array, a new kind of electrical stimulation of the retina prosthesis including dual information about the image (images that the existing technique can achieve are low-pixel images without color recognition ability) and the meaning of the scene content can be realized.

Additional aspects and advantages of the present application will be set forth in the descriptions hereinbelow, and some of them would become obvious from the following description or be appreciated from practice of the present application.

BRIEF DESCRIPTION OF THE DRAWINGS

In order to more clearly illustrate the embodiments of the present application or the technical solutions in the prior art, the drawings used in the embodiments or the description of the prior art will be briefly described below. Obviously, the drawings in the following description are only some of the embodiments of the present application, and other drawings may be obtained for those skilled in the art according to these drawings one the premise of not paying creative labors.

DETAILED DESCRIPTION

Embodiments of the present application provide a method and an apparatus for image recognition based on a retina prosthesis.

In order to make those skilled in the art better understand the technical solutions in the present application, the technical solutions in the embodiments of the present application will be clearly and completely described hereinbelow with reference to the accompanying drawings in the embodiments of the present application. The described embodiments are only a part of the embodiments of the present application, rather than all of the embodiments. All other embodiments obtained by those skilled in the art based on the embodiments of the present application without paying creative labor shall fall within the scope of the application.

Compared to research and development results of the existing retina prosthesis, the problems people facing is not to see the outline of the image any more, but how to quickly recognize complex scenes in a complex world, so that they may get in touch with the outside world in a more convenient, fast, and safe manner. The technical solutions of the present application propose the concept of setting a meaning area in an electrode array on the basis of the existing retina prosthesis structure, and a meaning prompt signal is transmitted to the corresponding retina through the electrode array of the meaning area so as to improve the information integrity in the complex scene faced by the patient.

Figure 1:
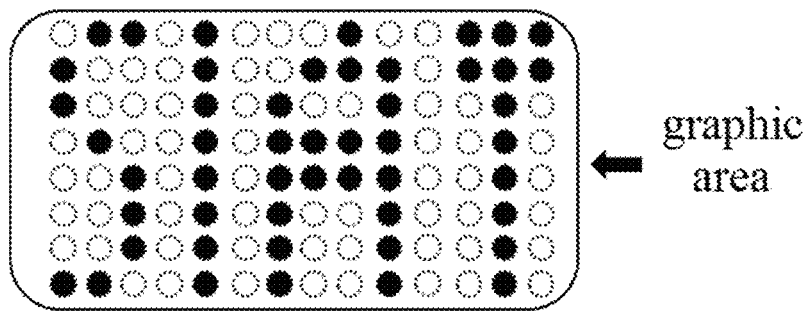
FIG. 1 is a schematic display view of image recognition of an existing retina prosthesis.
Figure 2:
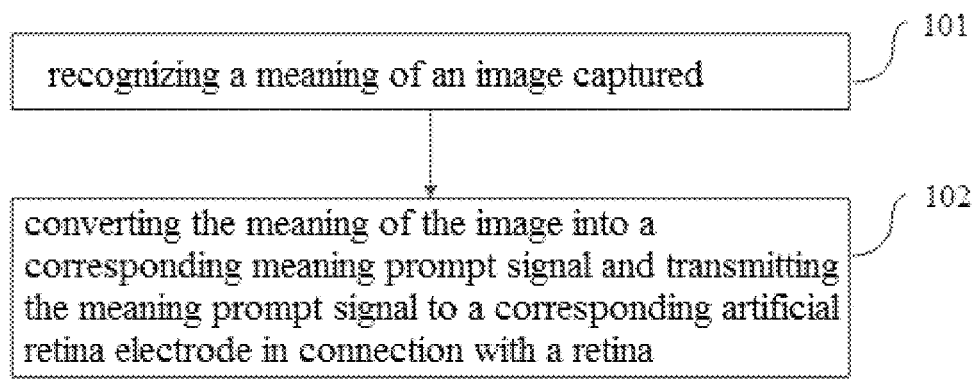
FIG. 2 is a schematic flow chart of a method for image recognition based on a retina prosthesis according to an embodiment of the present application.

FIG. 2 is a schematic flow chart of a method for image recognition based on a retina prosthesis provided by an embodiment of the present application, as shown in FIG. 2, the method comprises:

Step 101, recognizing meaning of an image captured; and

Step 102, converting the meaning of the image into a corresponding meaning prompt signal and transmitting the meaning prompt signal to a corresponding retina prosthesis electrode in connection with a retina.

The recognition of the meaning of the image includes, but is not limited to, color recognition, facial feature recognition, specific object recognition, and relative spatial position recognition, and other aspects. The facial feature recognition is, for example, recognizing a person by matching a facial feature with a preset facial feature. The specific objection recognition is, for example, distinguishing a person, a vehicle, an animal, etc. The relative spatial position recognition is, for example, identifying a relative distance or a relative position in relation to various objects.

Specifically, after the meaning of the image is recognized, the meaning of the image may be converted into the corresponding meaning prompt signal by a processor or other possible processing device such as a microchip, etc. The meaning prompt signal may be artificially set in advance. Specifically, for example, when red is seen, a corresponding electrode is stimulated; and when an animal is seen, another corresponding electrode is stimulated; or alternatively, a plurality of corresponding electrodes are stimulated at the same time to represent one meaning prompt signal, or one or multiple electrodes are stimulated with different frequencies and intensities to represent a certain meaning prompt signal. A variety of specific forms may be adopted, which are not listed herein.

After the meaning prompt signal is transmitted to the corresponding electrode in connection with the retina, the user can know the information in the current "seen" scene according to the meaning prompt signal received by the retina, which therefore assists in expanding the user's ability to recognize complex scenes. When used together with the image area of the electrode array, a new kind of electrical stimulation of the retina prosthesis including dual information about the image (images that the existing technique can provide are low-pixel images without color recognition ability) and the meaning of the scene content can be realized.

According to an embodiment of the present application, before said recognizing meaning of an image captured, the method further comprises: setting and storing a mapping relationship between the image and the meaning. Because different users may face different living scenes, and the mapping relationships between the images and the meanings are also different. Thus, the mapping relationship between the image and the meaning may be set in advance, and two kinds of meanings are recognized during the recognition of the meaning of a certain image, one kind is an universal meaning, that is, what is the captured image itself, for example, images with what features represent an animal, an object, or a person; and the other kind is a specific meaning, that is, images possessing what kind of features would correspond the user's father, friends, his own car, and so on. These two kinds of meanings may be recognized at the same time or recognized one after another according to a set priority. In addition, with the advancement of technology, in the recognition of the meanings of images, it is possible to recognize other types of meanings in the future, which fall within the protection scope of the technical solution of the present application.

According to an embodiment of the present application, before said converting the meaning of the image into a corresponding meaning prompt signal and transmitting the meaning prompt signal to a corresponding retina prosthesis electrode in connection with a retina, the method further comprises: setting and storing a mapping relationship between different meanings and meaning prompt signals. Specifically, after the meaning of the image is recognized, the meaning is converted into a meaning prompt signal according to a preset mapping relationship. The mapping relationship therebetween may be in one-to-one correspondence or may be in non-one-to-one correspondence, which can be set according to actual situation. The mapping relationship herein includes those mapping relationships implemented by defining the meaning represented by each electrode in advance, as well as those mapping relationships implemented by other ways which would be possible in the future.

According to an embodiment of the present application, said converting the meaning of the image into a corresponding meaning prompt signal and transmitting the meaning prompt signal to a corresponding retina prosthesis electrode in connection with a retina, specifically comprises: converting the meaning of the image into the corresponding meaning prompt signal; and stimulating a corresponding retina neuron by a corresponding electrode of a meaning area according to the meaning prompt signal. For example, the meaning area may be set in the electrode array of the retina prosthesis, electrode stimulations in the meaning area may represent different preset meanings, such that it would be possible to stimulate corresponding retina neutrons to output information of the meaning in the "seen" scene by stimulating electrodes of the meaning area with different meanings.

According to an embodiment of the present application, the meaning area is arranged at a specific area of an electrode array of the retina prosthesis. Specifically, for example, the meaning area is arranged at an edge of the electrode array of the retina prosthesis, including an upper edge, a lower edge, or a periphery edge of the retina, thereby enabling the user to remember the meaning represented by each electrode stimulation in the electrode array of the retina prosthesis.

By recognizing the color, the facial feature, the specific object, and the relative spatial position, and other meanings in the image, embodiments of the present application assist in expanding the user's ability to recognize complex scenes. When used together with the image area of the electrode array, a new kind of electrical stimulation of the retina prosthesis including dual information about the image (images that the existing technique can provide are low-pixel images without color recognition ability) and the meaning of the scene content can be realized.

Based on the same invention concept, embodiments of the present application further provides an apparatus for image recognition based on a retina prosthesis, which may be used to implement the methods described in the above embodiments, the apparatus is described in the following embodiments. Since the apparatus for image recognition based on a retina prosthesis has the same principle for solving the technical problems as the method for image recognition based on a retina prosthesis, the implementation of the apparatus for image recognition based on a retina prosthesis can refer to the implementation of the method for image recognition based on a retina prosthesis, and will therefore not repeated herein. As used hereinafter, the term "unit" or "module" may be a combination of software and/or hardware capable of implementing a predetermined function. Although the apparatus described in the following embodiments is preferably implemented in software, but the implementation in hardware or a combination of the software and the hardware is also possible and contemplated.

Figure 3:
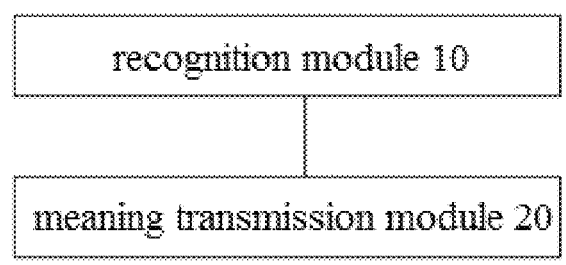
FIG. 3 is a schematic structural diagram of an apparatus for image recognition based on a retina prosthesis according to an embodiment of the present application.

FIG. 3 is a schematic structural view of an apparatus for image recognition based on a retina prosthesis according to an embodiment of the present application. The apparatus in this embodiment may comprise logic parts configured to implement corresponding functions, and may also be electronic devices operated by software of corresponding functions. As shown in FIG. 3, an apparatus for image recognition based on a retina prosthesis comprises: a recognition module 10 and a meaning transmission module 20.

Specifically, the recognition module 10 is configured to recognize meaning of an image captured. The recognition of the meaning of the image by the recognition module 10 includes, but is not limited to, color recognition, facial feature recognition, specific object recognition, and relative spatial position recognition, and other aspects. The facial feature recognition is, for example, recognizing a person by matching a facial feature with a preset facial feature. The specific objection recognition is, for example, distinguishing a person, a vehicle, an animal, etc. The relative spatial position recognition is, for example, identifying a relative distance or a relative position in relation to various objects.

The meaning transmission module 20 is configured to convert the meaning of the image into a corresponding meaning prompt signal and transmitting the meaning prompt signal to a corresponding retina prosthesis electrode in connection with a retina. Specifically, after the meaning of the image is recognized, the meaning of the image may be converted into the corresponding meaning prompt signal by a processor or other possible processing device such as a microchip, etc. The meaning prompt signal may be artificially set in advance. Specifically, for example, when red is seen, a corresponding electrode is stimulated; and when an animal is seen, another corresponding electrode is stimulated; or alternatively, a plurality of corresponding electrodes are stimulated at the same time to represent one meaning prompt signal. A variety of specific forms may be adopted, which are not listed herein.

After the meaning prompt signal is transmitted to the corresponding electrode in connection with the retina, the user can know the information in the current "seen" scene according to the meaning prompt signal received by the retina, which therefore assists in expanding the user's ability to recognize complex scenes. When used together with the image area of the electrode array, a new kind of electrical stimulation of the retina prosthesis including dual information about the image (images that the existing technique can provide are colorless, low-pixel images) and the meaning of the scene content can be realized.

Figure 4:
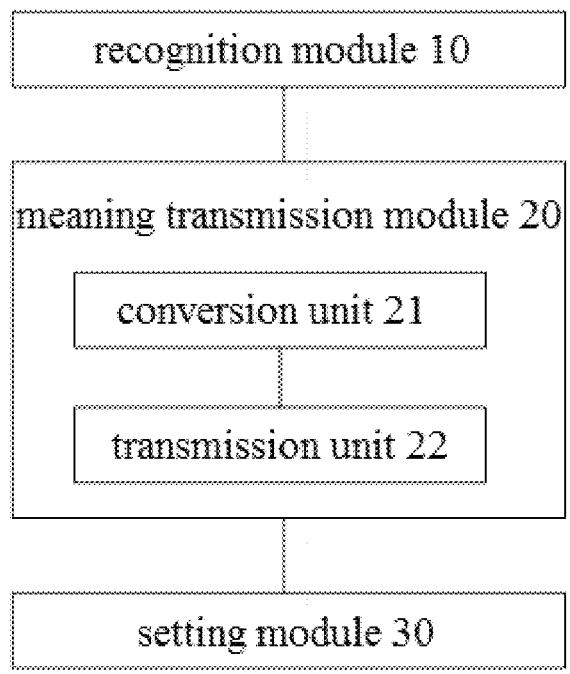
FIG. 4 is a schematic structural diagram of an apparatus for image recognition based on a retina prosthesis according to another embodiment of the present application.
Figure 5:
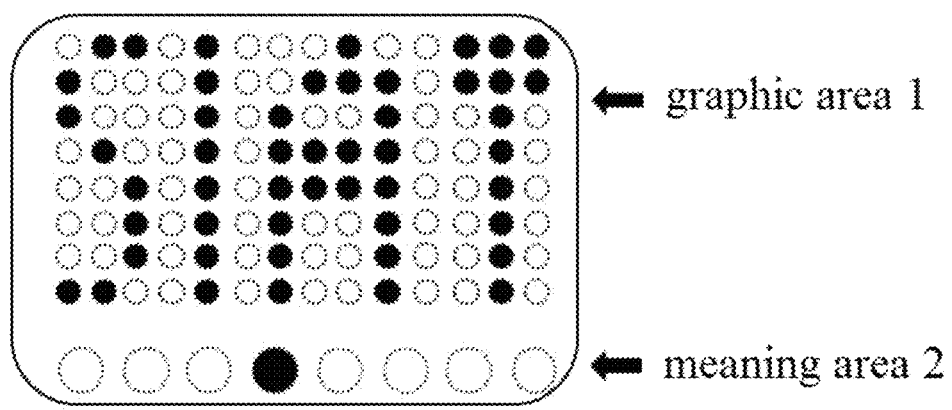
FIG. 5 is a schematic structural view of an electrode array combining a graphics area and a meaning area according to another embodiment of the present application.

FIG. 4 is a schematic structural view of an apparatus for image recognition based on a retina prosthesis according to another embodiment of the present application. As shown in FIG. 4, on the basis of FIG. 3, the apparatus further comprises: a setting module 30, a conversion unit 21, and a transmission unit 22, of which, the conversion unit 21 and the transmission unit 22 are comprised by the meaning transmission module 20.

Specifically, the setting module 30 is configured to set and store a mapping relationship between the image and the meaning.

According to an embodiment of the present application, the setting module 30 is further configured to set and store a mapping relationship between different meanings and meaning prompt signals.

According to an embodiment of the present application, the meaning prompt signal is transmitted to a corresponding retina neuron via a preset electrode of a meaning area, and the meaning transmission module 20 specifically comprises:

a conversion unit 21, configured to convert the meaning of the image into the corresponding meaning prompt signal; and a transmission unit 22, configured to stimulate the corresponding retina neuron by the corresponding electrode of the meaning area according to the meaning prompt signal.

According to an embodiment of the present application, the meaning area is arranged at a specific area of an electrode array of the retina prosthesis. The meaning area is arranged at an edge of the electrode array of the retina prosthesis. Specific position arrangement includes: an upper edge, a lower edge, and a periphery edge of the retina, thereby enabling the user to remember the meaning represented by each electrode stimulation in the electrode array of the retina prosthesis.

By recognizing the color, the facial feature, the specific object, and the relative spatial position and other meanings in the image, embodiments of the present application assist in expanding the user's ability to recognize complex scenes. When used together with the image area of the electrode array, a new kind of electrical stimulation of the retina prosthesis including dual information about the image (images that the existing technique can provide are low-pixel images without color recognition ability) and the meaning of the scene content can be realized.

In the following, in conjunction with the overall structure of the retina prosthesis, and taking an electrode array combining the graphic area 1 with the meaning area 2 as an example, the use of the retina prosthesis of the method and the apparatus of the present application in visual aid for user is illustrated as an example. Those the same or common parts as the above embodiments will not be explained in detail.

Assuming that a user using such a retina prosthesis is about to cross an intersection, he/she may be in touch with the following complex scene information:

1. traffic light color information;
2. acquaintance face recognition information;
3. distinguishing information on pedestrians, vehicles, and animals;

4. relative spatial position information of the above 1, 2, 3 relative to the patient himself/herself.

It is a very difficult problem to distinguish traffic lights, or to "see clearly" the acquaintances around, or to distinguish among pedestrians, vehicles, and animals, and perceive the relative location of these objects. Compared with the conventional retina prosthesis with the electrode array only having the graphics area, the new retina prosthesis of the present application based on the dual information of the image and meaning, the specific classification of the meaning area can include the following aspects:

1. Describing the content of the image by color recognition. Based on the electrodes of the graphic area, the meaning area can be further divided to include an electrode area for representing colors, which may correspond to colors such as red, yellow, and green. For example, yellow corresponds to a number 1 electrode stimulation of the meaning area, green corresponds to a number 2 electrode stimulation, and red corresponds to a number 3 electrode stimulation.

Specifically, the color area can define all colors, and can also define the appearance of various color blends according to actual conditions. For example, simultaneous stimulations of the number 2 and the number 3 electrodes represents the green-red color in the real world, and the of number 1, number 2, and number 3 electrode stimulations represent the mixed color of yellow, green, and red in the real world.

2. Describing the content of the image by face recognition. Based on the electrodes of the graphic area, the meaning area can be further divided to include an electrode area representing for facial features, which may correspond to father, mother, brother, and the like. For example, father corresponds to a number 4 electrode stimulation in the meaning area, mother corresponds to a number 5 electrode stimulation in the meaning area, and brother corresponds to a number 6 electrode stimulation in the meaning area.

Specifically, the face recognition area can define all facial features for recognition, and can also define a plurality of specific faces for recognition, etc. For example, the number 4 and number 5 electrode stimulations represent "seeing" father and mother. The number 4, number 5, and number 6 electrode stimulations represent "seeing" father, mother, and brother.

3. Describing the content of the image by specific object recognition. Based on the electrodes of the graphic area, the meaning area can be further divided to include the electrode area representing a specific object (human, animal, vehicle, etc.). For example, the humanoid recognition corresponds to a number 7 electrode stimulation in the meaning area, the animal recognition corresponds to a number 8 electrode stimulation, and the vehicle recognition corresponds to a number 9 electrode stimulation.

Specifically, the specific object recognition can define all objects for recognition, and can also define multiple/specific objects for recognition or simultaneous recognition. For example, the number 7 electrode stimulation and the number 8 electrode stimulation represent "seeing" humans and animals, while the number 7 electrode stimulation, the number 8 electrode stimulation, and the number 9 electrode stimulation represent "seeing" humans, animals, and vehicles.

4. Describing the content of the image (e.g. relative distance, relative position, etc.) by relative spatial position recognition. Based on the electrodes of the graphic area, the meaning area can be further divided to include the electrode area representing the relative spatial position. For example, it can be defined as follows:

Continuous strengthening or weakening of number 1, number 2, number 3, number 4, number 5, number 6, number 7, number 8, number 9 electrode stimulations represents the decrease or increase in the relative distance in the real world. Specifically, for example, the continuous strengthening of the number 8 electrode stimulation frequency represents that the animal is getting closer to the user, while the continuous strengthening of the number 9 electrode stimulation represents that the car is getting closer to the user.

Figure 6:
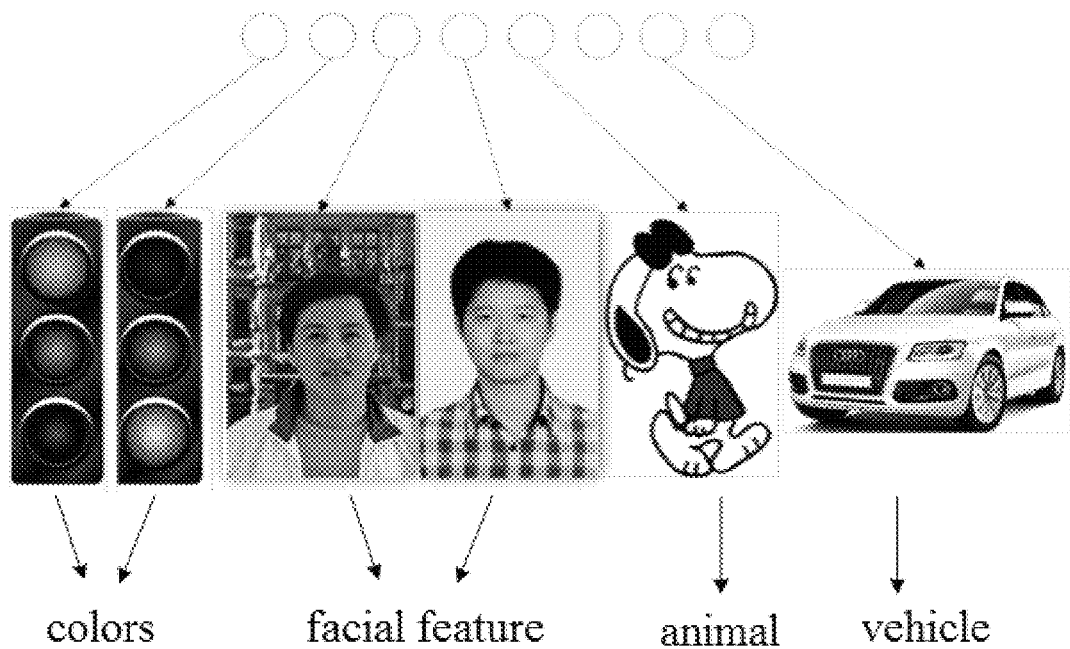
FIG. 6 is a schematic diagram of a correspondence relationship between a scene content that a user may be in touch and an electrode of a meaning area according to an embodiment of the present application.

In summary of the above, as shown in FIG. 6, a schematic diagram of a corresponding relationship between the scene content that the user may contact and the electrode of the meaning area electrode is shown.

It should be noted that the above-mentioned electrode stimulation scheme is merely exemplary, and the electrode array of the retina prosthesis has various stimulation modes for retina neuron, and multiple possible combinations may be further generated by combining the method and the apparatus of the present application with different electrode stimulation modes. Moreover, in practical applications, the electrodes of the meaning area are independent and at the same time related to each other, and various electrodes of the meaning area can simultaneously stimulate according to a corresponding meaning prompt signal, thereby being able to present the complex scene information of the outside world to blind persons.

Figure 7:
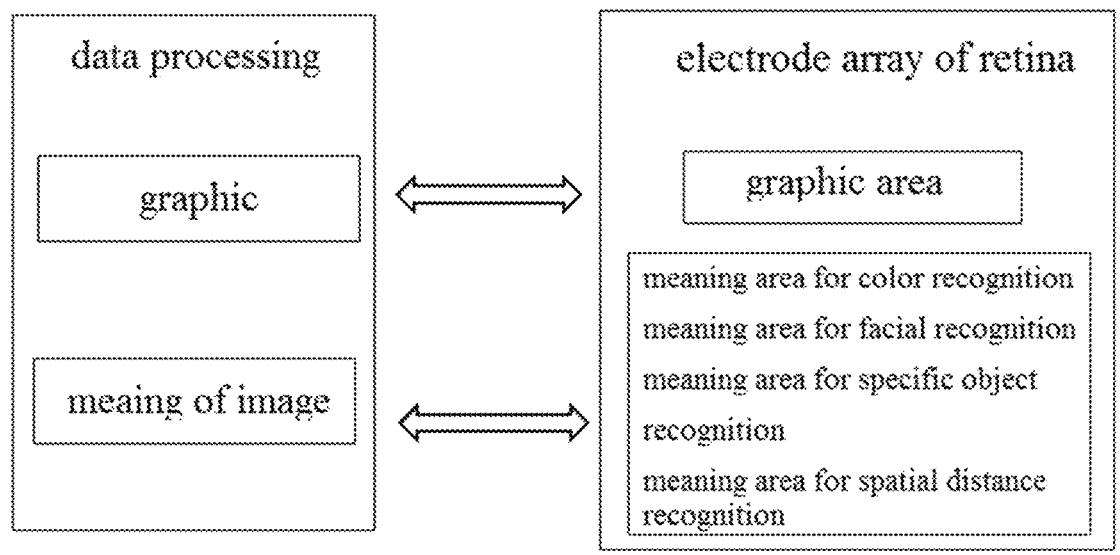
FIG. 7 is a schematic diagram showing the functional structures of a retina prosthesis applying a technical solution of the present application.

In a specific implementation process, as shown in FIG. 7, an external camera of the retina prosthesis captures an image, which is then processed by a data processing device to transmit a graphic itself to the electrode array of the retinal graphic area, the recognized meaning of the image is then transmitted to the electrode array of the retina meaning area, so as to produce corresponding stimulations on the retina.

It should be understood that after adopting the technical solution of the present application, the retina prosthesis can add the meaning area on the basis of the original graphic area stimulation scheme. After the image captured by an external device being processed by software algorithms, the meaning of the image of the external environment is extracted and output to the retina neuron through the meaning area.

In addition, the meaning area can be used together with the graphics area to supplement further information for the outline of the image, or it may also be used separately to directly transmit the meaning of the recognized image to the retina or other nerve cells with the same functions.

In a specific embodiment, the above retina prosthesis is preferably applied to patients with acquired retinal degenerative diseases. The meanings of the electrodes in the meaning area can be defined differently according to different needs of the patients. After the retina prosthesis is implanted into the patients, the meanings represented by corresponding electrode stimulation signal of the meaning area are trained for the users, so as to enable the user to better adapt to the retina prosthesis, and fully utilize of the prompting function of the meaning area, and at the same time realize the personalized setting of the retina prosthesis.

By recognizing the color, the facial feature, the specific object, and the relative spatial position and other meanings in the image, embodiments of the present application assist in expanding the user's ability to recognize complex scenes. When used together with the image area of the electrode array, a new kind of electrical stimulation of the retina prosthesis including dual information about the image (images that the existing technique can provide are low-pixel images without color recognition ability) and the meaning of the scene content can be realized. By setting the mapping relationship between the image and the meaning and the mapping relationship between the meaning prompt signal and the electrode stimulation, it is also possible to achieve personalized setting of the retina prosthesis, improve the quality of life of blind patients, and greatly improve the usability of retina prosthesis products.

Embodiments of the present application also provide a computer readable storage medium comprising computer readable instructions, which, when being executed, causes a processor to perform at least the following operations: recognizing meaning of an image captured; and converting the meaning of the image into a corresponding meaning prompt signal and transmitting the meaning prompt signal to a corresponding retina prosthesis electrode in connection with a retina.

Figure 8:
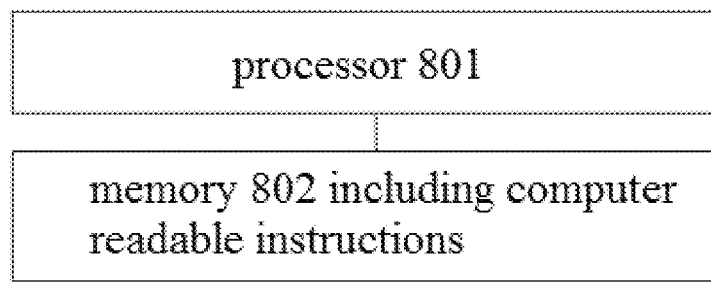
FIG. 8 is a device according to an embodiment of the present application.

An embodiment of the present application further provides an apparatus, as shown in FIG. 8, and the apparatus comprises: a processor 801 and a memory 802 including computer readable instructions, which, when being executed, cause a processor to execute the following operations: recognizing meaning of an image captured; and converting the meaning of the image into a corresponding meaning prompt signal and transmitting the meaning prompt signal to a corresponding retina prosthesis electrode in connection with a retina.

By recognizing the color, the facial feature, the specific object, and the relative spatial position and other meanings in the image, embodiments of the present application assist in expanding the user's ability to recognize complex scenes. When used together with the image area of the electrode array, a new kind of electrical stimulation of the retina prosthesis including dual information about the image (images that the existing technique can provide are low-pixel images without color recognition ability) and the meaning of the scene content can be realized. By setting the mapping relationship between the image and the meaning and the mapping relationship between the meaning prompt signal and the electrode stimulation, it is also possible to achieve personalized setting of the retina prosthesis, improve the quality of life of blind patients, and greatly improve the usability of retina prosthesis products.

It is to be noted that, in the description of the present application, the terms "first", "second", etc. are used for descriptive purposes only, but cannot be construed as indicating or implying relative importance. Further, unless otherwise indicated, the meaning of "multiple" or "a plurality of" in the description of the present application is two or more.

Any process or method description in the flowcharts or described in other manners herein can be understood as a module, a fragment, or a portion of code comprising one or more executable instructions for implementing steps of particular logical functions or processes, and the scope of the preferred embodiments of the present application includes additional implementations, in which the functions may be performed not according to the illustrated or discussed orders, including a substantially simultaneous manner according to functions involved and a reverse order. This should be understood by those skilled in the art to which the embodiments of the present application pertain.

It should be understood that portions of the present application can be implemented in hardware, software, firmware, or a combination thereof. In the above-described embodiments, multiple steps or methods may be implemented in software or firmware stored in a memory and executed by a suitable instruction execution system. For example, if implemented in hardware, as in another embodiment, it can be implemented by any one or combination of the following techniques well known in the art: discrete logic circuits with logic gates for implementing logic functions on data signals, application specific integrated circuits with suitable combinational logic gates, programmable gate arrays (PGAs), field programmable gate arrays (FPGAs), etc.

Those skilled in the art may understand that all or a part of the steps carried by the methods of the above-described embodiments may be accomplished by instructing related hardware by a program, and the program may be stored in a computer readable storage medium. The program, when being executed, includes one or a combination of the steps of the method embodiments.

In the description of the present specification, the description with reference to the terms "an embodiment", "some embodiments", "example", "specific example", or "some examples", etc., is meant to be described specific features, structures, materials, or characteristics described in connection with the embodiment or example are included in at least one embodiment or example of the application. In the present specification, the illustrative expression of the above terms does not necessarily mean the same embodiment or example. Furthermore, the particular features, structures, materials, or characteristics described may be combined in a suitable manner in any one or more embodiments or examples.

While the embodiments of the present application have been shown and described in the above, it can be understood that the above-described embodiments are illustrative and cannot to be construed as limiting the scope of the present application. Those skilled in the art may make changes, modifications, substitutions, and variations to the above-described embodiments within the scope of the present application.

What is claimed is:

1. A method for image recognition based on a retina prosthesis, comprising:
   providing a retina prosthesis, wherein the retina prosthesis comprises an electrode array, the electrode array comprises: a graphic area, configured to percept a contour information of an image captured, and a meaning area, configured to percept a meaning of the image captured, the meaning of the image comprising: colors, facial features, specific objects, and relative spatial positions; and wherein different electrode stimulations in the meaning area indicative of corresponding meanings are self-defined as meaning prompt signals in advance and remembered by a user;
   recognizing the meaning of the image captured; and
   converting the meaning of the image into the corresponding meaning prompt signal based on the electrode stimulation indicative of the meaning, and transmitting the meaning prompt signal to a corresponding electrode of the meaning area in connection with a retina.

2. The method of claim 1, further comprising, before said recognizing meaning of an image captured:
   setting and storing a mapping relationship between the image and the meaning.

3. The method of claim 2, wherein said converting the meaning of the image into the corresponding meaning prompt signal based on the electrode stimulation indicative of the meaning, and transmitting the meaning prompt signal to a corresponding electrode of the meaning area in connection with a retina, comprises:
   converting the meaning of the image into the corresponding meaning prompt signal; and stimulating a corresponding electrode of the meaning area according to the meaning prompt signal thereby stimulating a corresponding retina neuron.

4. The method of claim 1, before said converting the meaning of the image into the corresponding meaning prompt signal based on the electrode stimulation indicative of the meaning, and transmitting the meaning prompt signal to a corresponding electrode of the meaning area in connection with a retina, further comprising:

self-defining and storing a mapping relationship between different meanings and meaning prompt signals.

5. The method of claim 4, wherein converting the meaning of the image into the corresponding meaning prompt signal based on the electrode stimulation indicative of the meaning, and transmitting the meaning prompt signal to a corresponding electrode of the meaning area in connection with a retina, comprises:

converting the meaning of the image into the corresponding meaning prompt signal; and stimulating a corresponding electrode of the meaning area according to the meaning prompt signal thereby stimulating a corresponding retina neuron.

6. The method of claim 1, wherein said converting the meaning of the image into the corresponding meaning prompt signal based on the electrode stimulation indicative of the meaning, and transmitting the meaning prompt signal to a corresponding electrode of the meaning area in connection with a retina, comprises:

converting the meaning of the image into the corresponding meaning prompt signal; and stimulating a corresponding electrode of the meaning area according to the meaning prompt signal thereby stimulating a corresponding retina neuron.

7. The method of claim 6, wherein the meaning area is arranged at a specific area of an electrode array of the retina prosthesis.

8. The method of claim 7, wherein the meaning area is arranged at an edge of the electrode array of the retina prosthesis.

9. The method of claim 1, wherein the meaning area comprises: color perception region, facial perception region, specific object perception region, and spatial distance perception region.

10. An apparatus for image recognition based on a retina prosthesis, comprising:

a retina prosthesis, wherein the retina prosthesis comprises an electrode array, the electrode array comprises:

a graphic area, configured to percept a contour information of an image captured, and a meaning area, configured to percept a meaning of the image captured; wherein the meaning of the image comprises: colors, facial features, specific objects, and relative spatial positions; and wherein different electrode stimulations in the meaning area indicative of corresponding meanings are self-defined as meaning prompt signals in advance and remembered by a user;

a recognition module, configured to recognize the meaning of the image captured and a meaning transmission module, configured to convert the meaning of the image into the corresponding meaning prompt signal based on the electrode stimulation indicative of the meaning, and transmit the meaning prompt signal to a corresponding electrode of the meaning area in connection with a retina.

11. The apparatus of claim 10, further comprising:

a setting module, configured to set and store a mapping relationship between the image and the meaning.

12. The apparatus of claim 11, wherein the setting module is further configured to set pre-define and store a mapping relationship between different meanings and meaning prompt signals.

13. The apparatus of claim 12, wherein the meaning prompt signal is transmitted to a corresponding retina neuron via the self-defined electrode stimulations of the meaning area, and the meaning transmission module comprises:

a conversion unit, configured to convert the meaning of the image into the corresponding meaning prompt signal; and a transmission unit, configured to stimulate the corresponding electrode of the meaning area according to the meaning prompt signal thereby stimulating the corresponding retina neuron.

14. The apparatus of claim 13, wherein the meaning area is arranged at a specific area of an electrode array of the retina prosthesis.

15. The apparatus of claim 14, wherein the meaning area is arranged at an edge of the electrode array of the retina prosthesis.

16. The apparatus of claim 10, wherein the meaning area comprises: color perception region, facial perception region, specific object perception region, and spatial distance perception region.

* * * * *